(12) United States Patent
Jeong et al.

(10) Patent No.: US 6,994,862 B2
(45) Date of Patent: Feb. 7, 2006

(54) FORMULATION SOLUBILIZING WATER-INSOLUBLE AGENTS AND PREPARATION METHOD THEREOF

(75) Inventors: Seo Young Jeong, Koyang-shi (KR); Ick Chan Kwon, Seoul (KR); Hesson Chung, Incheon (KR)

(73) Assignee: Korea Institute of Science and Technology, Seoul (KR)

( * ) Notice: Subject to any disclaimer, the term of this patent is extended or adjusted under 35 U.S.C. 154(b) by 293 days.

(21) Appl. No.: 10/221,449

(22) PCT Filed: Mar. 13, 2001

(86) PCT No.: PCT/KR01/00389

§ 371 (c)(1),
(2), (4) Date: Sep. 12, 2002

(87) PCT Pub. No.: WO01/68139

PCT Pub. Date: Sep. 20, 2001

(65) Prior Publication Data

US 2003/0099675 A1 May 29, 2003

(30) Foreign Application Priority Data

Mar. 13, 2000 (KR) ........................................ 2000-12465

(51) Int. Cl.
*A61K 7/00* (2006.01)

(52) U.S. Cl. ...................................... 424/401; 424/489
(58) Field of Classification Search ................ 424/401, 424/489

See application file for complete search history.

(56) References Cited

U.S. PATENT DOCUMENTS

| 5,438,072 A | 8/1995 | Bobee et al. |
| 5,531,925 A | 7/1996 | Landh et al. |
| 5,958,876 A | 9/1999 | Woo |
| 6,214,375 B1 * | 4/2001 | Modi .......................... 424/450 |
| 6,248,363 B1 * | 6/2001 | Patel et al. .................. 424/497 |
| 6,531,139 B1 * | 3/2003 | Gao et al. .................... 424/400 |
| 6,569,478 B1 | 5/2003 | Leser et al. |

FOREIGN PATENT DOCUMENTS

| WO | WO 99/06024 | 2/1999 |
| WO | WO 99/06043 | 2/1999 |
| WO | WO 99/47004 | 9/1999 |

* cited by examiner

*Primary Examiner*—Shelley A. Dodson
*Assistant Examiner*—Konata M. George
(74) *Attorney, Agent, or Firm*—Finnegan, Henderson, Farabow, Garrett & Dunner, LLP (57) ABSTRACT

The present invention relates to an anhydrous liquid composition wherein monoglyceride is mixed with an emulsifier and a solvent, and the manufacturing method thereof, and more specifically, to an anhydrous liquid composition wherein monoglyceride is mixed with a water-insoluble material, an emulsifier and a solvent, and the manufacturing method thereof. Further, the present invention relates to a lyophilized powder and the manufacturing method thereof, wherein the lyophilized powder is prepared by dissolving the mixed liquid composition in water, adding with a cryoprotectant followed by the lyophilization. In the process of dispersion, the lyophilized liquid composition and the powder of the present invention can spontaneously generate particles of 200–500 nm by gently shaking with hands without a powerful mechanical force. Also the lyophilized liquid composition and the powder of the present invention are physicochemically stable since they neither contain water that causes oxidation or hydrolysis upon storage nor undergo phase separation. Considering all the raw materials of the present invention are biocompatible, the present invention will be useful in medical and pharmaceutical fields such as drug delivery.

30 Claims, 1 Drawing Sheet

FORMULATION SOLUBILIZING WATER-INSOLUBLE AGENTS AND PREPARATION METHOD THEREOF

BACKGROUND OF THE INVENTION

1. Field of the Invention

The present invention relates to a novel solubilizing composition, its liquid and powder formulations, its liquid and powder formulations containing pharmaceutical compounds, and the preparation method thereof wherein said solubilizing composition comprises 9~90% by weight of at least one selected from the monoglycerides, 0.01~90% by weight, of at least one emulsifier, and 0~90.9% by weight of an organic solvent.

2. Description of the Related Art

Solubilization of materials can be applied to a variety of fields. In chemical processing where their catalysts, reactants, intermediates, etc. are water-insoluble materials, the solubilization of these materials will affect the yield and the direction of a given reaction. Numerous pharmaceutical compounds with good physiological activities are known to be insoluble in water and thus they have relatively low bioavailabilities. Because the solubilization of these pharmaceutical compounds can simplify administration routes and increase pharmaceutical effects, the solubilization technology is essential in commercializing water-insoluble pharmaceuticals, and therefore extensive worldwide studies have been focused on developing the solubilization technology. Cyclosporin and paclitaxel (Taxol®), for instance, are good Examples of water-insoluble pharmaceutical compounds that cannot be administered alone due to their low solubilities. The solubilizing technology, therefore, has been developed simultaneously with the development of these pharmaceutical compounds themselves. Cyclosporin and paclitaxel are commercially available as pre-concentrates of Cremophor emulsion. These formulations can spontaneously form microemulsion upon dispersion in water (U.S. Pat. No. 5,438,072).

In general, solubilizing formulations include emulsion or liposome, which uses lipid as a medium, and a polymeric nanoparticle or polymeric micelle, which uses a polymer as a medium (Langer, R. Nature, 392, 5–10, 1998). Of these, the formulations using lipid as a medium are relatively advantageous in that their raw materials are biocompatible and thus they can be widely applied to medical fields including drug delivery systems. In particular, the emulsions are heterogeneous mixture of oil and water by the use of emulsifiers. The oil-in-water type emulsions, composed of oil components dispersed in water, are widely used in solubilizing water-insoluble pharmaceutical compounds. Liposome formulations consist of spherical lipid vesicles with lipid bilayers and water-insoluble pharmaceutical compounds are enclosed within the lipid bilayer.

U.S. Pat. No. 5,531,925 discloses Cubosome, another type of formulation using lipid as a solubilization medium, which was first developed by Swedish scientists in early 1990s. Cubosome is prepared by dispersing the hydrated lipid cubic phase in water. The interior of Cubosome comprises cubic phase wherein lipid and water components constitute continuous but separate three-dimensional channels, and there exists an interface between lipid head-group and water. Therefore, Cubosome could be advantageous over the conventional emulsion type or liposome type formulations, which only allow solubilization of hydrophobic and hydrophilic pharmaceutical compounds, respectively, in that they can solubilize amphiphilic pharmaceutical compounds as well as hydrophobic and hydrophilic pharmaceutical compounds.

Cubosomes can be formed by first forming a very viscous liquid cubic phase by adding water and an emulsifier to monoglyceride, and then by dispersing the mixture in water. Cubosome has average particle size of as large as several micrometers in diameter with the aid of emulsifiers. Since it is preferential to have submicron-sized particles for the solubilization of pharmaceutical compounds, it is also possible to obtain submicron-sized particles by applying mechanical forces such as microfluidization.

Preparing submicron-sized cubosome particles by means of a mechanical force, however, may result in physicochemical instability of the enclosed materials or the constituting ingredients of the formulations due to high energy and high temperature accompanying the mechanical process. The formulation process may also incur hydrolysis and oxidization of constituting ingredients because the enclosed materials or the constituting ingredients of the formulations may be vigorously mixed with air during the microfluidization process. Moreover, the dispersed cubosomes prepared by the microfluidization process may experience the instability of the dispersion system after a prolonged storage and subsequently result in phase separation due to aggregation of particles. Although cubosome type formulations have adventageous properties as described above over the conventional type of formulations, they also have disadvantages that they cannot encapsulate the thermally labile pharmaceutical compounds. Also, the physical and chemical stability of the formulation need to be improved greatly to provide a successful drug delivery system.

SUMMARY OF THE INVENTION

After intensive studies to solve the above problems, the inventors of the present invention finally succeeded in preparing a homogeneous liquid formulation comprising monoglycerides, emulsifiers and organic solvents. This liquid formulation can be easily dispersed in water, without using a harsh physical force, to form a dispersion of particles of less than 500 nm. The homogeneous liquid formulation is physically stable since it is a single phase liquid, and also chemically stable since it does not contain water and does not require physical force during the formulation process. The liquid formulation of the present invention, therefore, can be stored for a prolonged period of time.

Therefore, the object of the present invention is to provide a novel solubilizing composition, which enables stable solubilization of materials as well as stable long-term storage, and the manufacturing method thereof.

Another object of the present invention is to provide a liquid formulation and a powder formulation for said solubilizing composition, and the manufacturing method thereof.

Still another object of the present invention is to provide a liquid formulation and a powder formulation for said solubilizing composition to be used in drug delivery system wherein pharmaceutical compounds are added, and the manufacturing method thereof.

DETAILED DESCRIPTION OF THE INVENTION

The present invention relates to a solubilizing composition comprising 9~90% by weight of at least one monoglyceride, 0.01~90% by weight of at least one emulsifier, and 0~90.9% by weight of an organic solvent. The above composition is prepared by dissolving at least one monoglyceride compound and an emulsifier in an organic solvent followed by removing the organic solvent.

The monoglyceride compound is preferred to select at least one from saturated or unsaturated $C_{10}$–$C_{22}$ monoglycerides. The monoglyceride compound used in the present invention is monoolein, monopalmitolein, monomyristolein, monoeladin, and monoerucin, and more preferably monoolein.

The emulsifier is preferred to select from the group consisting of phospholipid, a non-ionic surfactant, an anionic surfactant, a cationic surfactant, and bile acid.

The phospholipid is preferred to select from the group consisting of a phosphatidylcholine (PC) and its derivative, a phosphatidylethanolamine (PE) and its derivative, a phosphatidylserine (PS) and its derivative or a polymeric lipid wherein a hydrophilic polymer is conjugated to the lipid headgroup.

The non-ionic surfactant is selected from the group consisting of a poloxamer (also known as Pluronic: polyoxyethylene-polyoxypropylene copolymer), a sorbitan ester (Span), a polyoxyethylene sorbitan (Tween) or a polyoxyethylene ether (Brij).

The anionic surfactant is selected from the group consisting of a phosphatidylserine (PS) and its derivative, a phosphatidic acid (PA) and its derivative or sodium dodecyl sulfate (SDS).

The cationic surfactant is selected from the group consisting of 1,2-dioleyl-3-trimethylammonium propane (DOTAP), dimethyldioctadecylammonium bromide (DDAB), N-[1-(1,2-dioleyloxy)propyl]-N,N,N-trimethylammonium chloride (DOTMA), 1,2-dioleyl-3-ethylphosphocholine (DOEPC) or 3β-[N-[(N',N'-dimethylamino)ethan]carbamoyl]cholesterol (DC-Chol).

The bile acid is selected from the group consisting of cholic acid, its salt and derivatives; deoxycholic acid, its salt and derivatives; chenocholic acid, its salt and derivatives; ursodeoxycholic acid, its salt and derivatives; and lithocholic acid, its salt and derivatives.

The organic solvent is preferred to select from the group consisting of alcohol, ethylene glycol, propylene glycol, polyethylene glycol (PEG), dimethylsulfoxide (DMSO) or the mixture of these solvents. The organic solvents such as acetone, chloroform, benzene, toluene, acetonitrile, alcohols or the mixture of these solvents, which dissolve both a lipid emulsifier and a water-insoluble compound, can also be used.

Other additives can be added to the above composition to be within 5% by weight and the Examples are fatty acids, fatty acid esters and fatty acid alcohols.

The present invention relates to a liquid formulation of the above solubilizing composition.

The liquid formulation of the present invention comprises 9~90% by weight of at least one monoglyceride, 0.01~90% by weight of at least one emulsifier, and 9~90.9% by weight of an organic solvent. The above liquid formulation is manufactured by mixing 1~99% by weight of the above solubilizing composition with 1~99% by weight of an organic solvent. More specifically, the method of manufacturing the above liquid formulation comprises (a) completely dissolving at least one monoglyceride compound and at least one emulsifier in an organic solvent and removing the organic solvent; and (b) preparing a homogeneous liquid phase by mixing the composition in the above step (a) with an organic solvent.

In the above step (a), an organic solvent is preferred to select from the group consisting of alcohol, chloroform, benzene, toluene, acetonitrile or the mixture of these solvents, and more preferably ethanol.

In the above step (b), an organic solvent is preferred to select from the group consisting of alcohol, ethylene glycol, propylene glycol, polyethylene glycol (PEG), dimethylsulfoxide (DMSO) or the mixture of these solvents. The organic solvents such as acetone, chloroform, benzene, toluene, acetonitrile, alcohols or the mixture of these solvents, which dissolve both a lipid emulsifier and a water-insoluble compound, can also be used.

An Example of manufacturing the above liquid formulation is as follows. First, one or more monoglycerides and one or more emulsifiers are completely dissolved in an organic solvent such as ethanol, and then the solvent is evaporated either by heating at about 40° C. under a nitrogen atmosphere or by applying a low atmospheric pressure. Here, a trace amount of ethanol that may be still present in the mixture does not affect the property of the final formulation. To this viscous liquid, i.e., the solubilizing composition, a solvent such as ethanol, propylene glycol, ethylene glycol, polyethylene glycol, dimethylsulfoxide (DMSO), is added to prepare a homogeneous mixed liquid formulation.

The present invention relates to manufacturing of a powder formulation by lyophilizing the dispersion of the above liquid formulation.

The above powder formulation is manufactured by dissolving the above liquid formulation, which comprises 9~90% by weight of at least one monoglyceride compound, 0.01~90% by weight of at least one emulsifier, and 9~90.9% by weight of an organic solvent, in excess water followed by lyophilization. More specifically, the method of manufacturing the above powder formulation comprises the steps of (a) dispersing the liquid formulation in excess water; and lyophilizing said dispersed liquid in step (b) by selectively adding a cryoprotectant.

A cryoprotectant may be used to prevent the morphological changes of the particles in the dispersion of the above formulation during lyophilization, and it is preferred to add it less than 30% (w/v) to the liquid formulation. Preferred Examples of a cryoprotectant include sugars such as mannitol or trehalose, amino acids such as arginine, and proteins such as albumin.

The present invention relates to the utilization of the solubilizing liquid formulation in the drug delivery system for water-insoluble or amphiphilic compounds. In particular, the present invention relates to solubilizing liquid formulations and powder formulations, and the manufacturing method thereof.

The solubilizing liquid formulation comprises 9~90% by weight of at least one monoglyceride compound, 0.01~90% by weight of at least one emulsifier, 0.001~50% by weight of a pharmaceutical compound and 9~90.9% by weight of an organic solvent.

The kinds of monoglyceride compound, an emulsifier and an organic solvent are the same as described above.

The above solubilizing formulations can enclose a hydrophilic, a hydrophobic and an amphiphilic compound as a pharmaceutical compound. Examples of these pharmaceutical compounds that can be used in the present invention are antivirals, steroidal anti-inflammatory drugs (SAID), non-steroidal anti-inflammatory drugs (NSAID), antibiotics, antifungals, vitamins, hormones, retinoic acid, prostaglandins, prostacyclins, anticancer drugs, antimetabolitic drugs, miotics, cholinergics, adrenergic antagonists, anticonvulsants, antianxiety agents, major tranquilizers, antidepressants, anesthetics, analgesics, anabolic steroids, estrogens, progesterones, glycosaminoglycans, polynucleotides, immunosuppressants and immunostimulants. In particular, pharmaceutical compounds such as cyclosporin A and paclitaxel, an immunosuppressant and an anticancer drug, which are generally hard to be solubilized can be readily solubilized in the present invention.

The solubilizing liquid formulations containing the above-mentioned pharmaceutical compounds can enclose 5% by weight or less of other conventional additives including fatty acids and ester derivatives thereof and alcohol derivatives thereof.

The method of manufacturing solubilizing liquid formulations containing the above-mentioned pharmaceutical compounds comprises (a) dissolving at least one monoglyceride compound, at least one pharmaceutical compound and at least one emulsifier in an organic solvent and removing the organic solvent; and (b) preparing a homogeneous liquid phase by mixing the composition in the above step (a) with an organic solvent.

In the above step (a), the preferred organic solvents are alcohol, chloroform, benzene, toluene, acetonitrile or the mixture of these solvents, and more preferably ethanol.

In the above step (b), the preferred organic solvents are alcohol, ethyleneglycol, propylene glycol, polyethyleneglycol, dimethylsulfoxide (DMSO) or the mixture of these solvents. The organic solvents such as acetone, chloroform, benzene, toluene, acetonitrile, alcohols or the mixture of these solvents, which dissolve both a lipid emulsifier and a water-insoluble compound, can also be used.

An Example of manufacturing the above liquid formulation is as follows. First, a monoglyceride compound and an emulsifier are completely dissolved in a solvent such as ethanol and then the solvent is evaporated either by heating at about 40° C. under a nitrogen atmosphere or by applying low atmospheric pressure. Here, a trace amount of ethanol that may be still present in the mixture does not affect the property of the final formulation. To this viscous liquid, in other words, the solubilizing composition, is added with an equal amount of solvent such as ethanol, ethylene glycol, propylene glycol, polyethylene glycol, dimethylsulfoxide (DMSO), and a homogeneous mixed liquid formulation is finally prepared.

The present invention is related to manufacturing of a water-insoluble solubilizing powder formulation containing a pharmaceutical compound by lyophilization of the dispersion prepared with the above solubilizing liquid formulation containing water-insoluble materials.

The above powder formulation comprises. The method of manufacturing the above powder formulation comprises the steps of (a) dispersing the liquid formulation comprising 9~90% by weight of at least one monoglyceride compound, 0.01~90% by weight of at least one emulsifier, 0.001~50% by weight of a pharmaceutical compound and 9~90.9% by weight of an organic solvent in excess water; and lyophilizing said dispersed liquid in step (b) by selectively adding a cryoprotectant.

A cryoprotectant may be used to prevent the morphological changes in the dispersion of the above formulation during lyophilization, and it is preferred to add it less than 30% (w/v) to the liquid formulation. Preferred Examples of a cryoprotectant include sugars such as mannitol or trehalose, amino acids such as arginine, and proteins such as albumin.

The above formulation of the present invention can be easily dispersed in water mediated by such a minimal mechanical aid as a simply shaking with hands. The size of particles is approximately 200~500 nm in general and varies depending on the property of a given pharmaceutical compounds or an emulsifier. Moreover, the constituting ingredients of and pharmaceutical compound in the particles are not degraded since a strong mechanical force is not required in generating the particles.

The formulations according to the present invention can be stored at room temperature in a sealed state for a long period of time without undergoing phase separation or the change in properties of the formulations. When a long-term storage is required, the powder formulation is desirable because it does not contact with an organic solvent or moisture.

Figure 1:
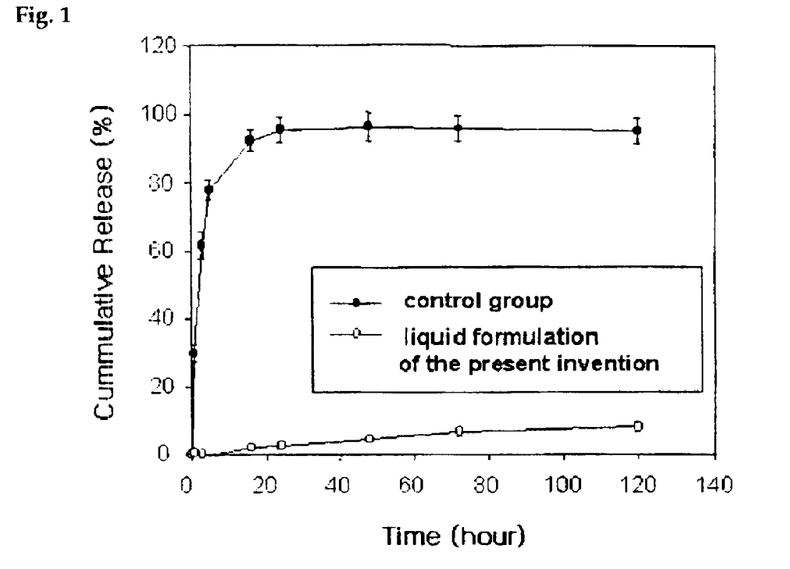
FIG. 1 is a graph that shows the release profile of a liquid formulation containing rifampicin (○: the present invention, ●: control Group).
Figure 2:
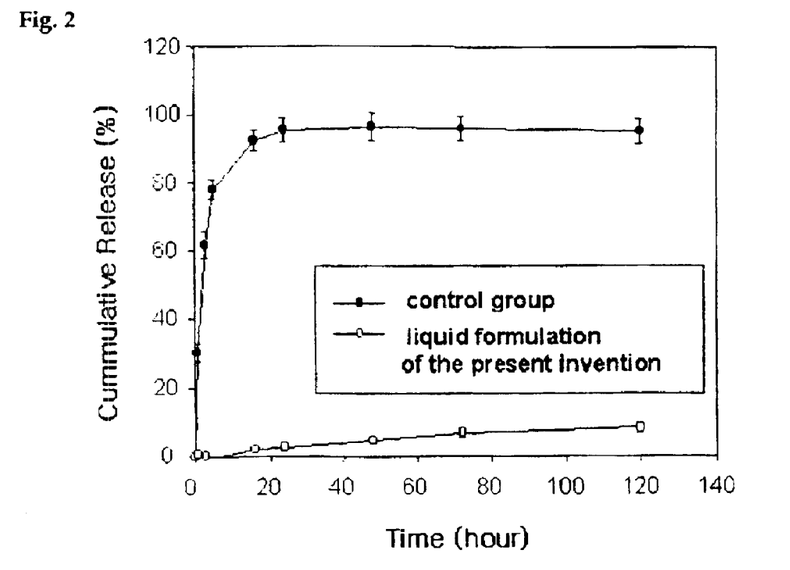
FIG. 2 is a graph that shows the release profile of a liquid formulation containing bromocresol green (○: the present invention, ●: control Group).

The formulations according to the present invention are useful in drug delivery system because they exhibit a sustained drug release pattern (FIGS. 1 and 2). When applying these formulations in drug delivery system, it is preferred to use various administration routes including intravenous injection, mucosal administration, buccal administration and nasal administration, and more preferably an oral administration.

This invention is explained in more detail based on the following Examples but they should not be construed as limiting the scope of this invention.

EXAMPLE 1

Liquid Formulation Manufactured According to the Change in the Amount of an Emulsifier (1)

(1) Manufacturing Solubilizing Composition

One hundred milligrams of monoolein and 15, 20, 25, 30, 35 and 40 mg each of Pluronic F-127 were added to about 1 mL of ethanol and dissolved completely. Ethanol in the mixture was evaporated by stirring under nitrogen atmosphere or by applying low pressure. Trace amount of ethanol still remaining in the above mixture did not affect the manufacturing of formulations.

(2) Manufacturing Liquid Formulation

In the prepared solubilizing compositions in the above step (1), 115, 120, 125, 130, 135 and 140 mg of ethanol, respectively, was added so that the final concentration of the ethanol in the resulting mixture can be about 50% (w/w). The mixture was shaken manually or set aside to be dissolved completely to prepare the liquid formulation.

(3) Property Analysis of thus Prepared Liquid Formulation

The size of the emulsion particles were measured by using Malvern Zetasizer (Malvern Instruments Limited, England) after diluting the emulsion by adding 3 mL of distilled water with 2 μL of thus obtained liquid formulation. An average particle size and polydispersity was obtained by measuring a given formulation three times (Orr, Encyclopedia of emulsion technology, 1, 369–404, 1985). This method was used in measuring the particle size and the polydispersity throughout the following Examples.

The above liquid formulations were dispersed well in water, and the average particle size was about 250 nm in diameter.

Meanwhile, each of the solubilizing compositions manufactured the same as in the above step (1) of Example 1 as a control group was added with an excessive amount of distilled water in place of an organic solvent. As a result, a gel with a strong viscosity was formed, and also shown to have an isotropic structure when observed under a polarized light microscope. Determination of the particle size was not possible because the formulation was not dispersed in water. Rather, the formulation formed a viscous gel that floats in water.

EXAMPLE 2

Liquid Formulation Manufactured According to the Change in the Amount of an Emulsifier (2)

The liquid formulations and dispersed liquid were prepared the same as in the step (1) of the Example 1 and their particle size and polydispersity were measured by the same methods in the Example 1 with the exception that 115, 120, 125, 130, 135 and 140 mg of PEG400, respectively, was added instead of ethanol to the solubilizing compositions obtained in the above step (1) so that the final concentration of the PEG400 in the resulting mixture can be about 50% (w/w). In this case, the above formulations were dispersed well in water, and the particle size was about 250 nm.

EXAMPLE 3

Liquid Formulation Manufactured According to the Change in the Amount of an Emulsifier (3)

The liquid formulations and dispersed liquid were prepared the same as in the step (1) of the Example 1 and their particle size and polydispersity were measured by the same methods in the Example 1 with the exception that 269, 280, 292 and 303 mg of propylene glycol, respectively, was added instead of ethanol to the solubilizing compositions obtained in the above step (1) so that the final concentration of the PEG400 in the resulting mixture can be about 70% (w/w). In this case, the above formulations were dispersed well in water and the particle size was about 350 nm.

The results of the Examples 1–3 are summarized in the following Table 1.

TABLE 1

| Pluronic F-127 (mg) | Solvents | | | |
| --- | --- | --- | --- | --- |
| | Water(control) | Ethanol | PEG400 | Propylene glycol |
| | Average Particle Size (nm)/Polydispersity | | | |
| 15 | Not dispersed | 258.0/0.123 | 278.0/0.290 | 312.1/0.257 |
| 20 | Not dispersed | 254.4/0.069 | 249.3/0.219 | 399.1/0.996 |
| 25 | Not dispersed | 259.3/0.345 | 277.9/0.428 | 351.3/0.320 |
| 30 | Not dispersed | 262.7/0.376 | 246.1/0.611 | 336.8/0.356 |
| 35 | Not dispersed | 274.7/0.367 | 248.1/0.071 | — |
| 40 | Not dispersed | 288.8/0.167 | 262.2/0.396 | — |

As a result, the formulations did not dissolve in water when an organic solvent was not added to the liquid formulations, and the formulations according to the present invention can be easily dispersed into particles less than 400 nm.

EXAMPLE 4

Liquid Formulation Manufactured According to the Change in the Amount of a Solvent (1)

(1) Manufacturing Solubilizing Composition

Ten milligrams of monoolein and 1.5 mg of Pluronic F-127 were added to about 0.1 mL of ethanol and dissolved completely. The ethanol in the mixture was evaporated by stirring under nitrogen atmosphere or by applying low pressure. Trace amount of ethanol still remaining in the above mixture did not affect the manufacturing of formulations.

(2) Manufacturing Liquid Formulation

In each of the prepared 11.5 mg of solubilizing compositions in the above step (1), 6.25, 9.5, 14.5, 22.0, 34.0, 57.5, and 129.5 μL of ethanol was added so that the final concentration of the ethanol in the resulting mixture can be about 50% (w/w). The mixture was shaken manually or set aside to be dissolved completely to prepare the liquid formulation. Three milliliters of distilled water was added to 2 μL of thus obtained liquid formulation and mixed well by shaking. The size of the particles as well as polydispersity of the dispersion was determined. The above liquid formulations were well dispersed in water when more than 9.5 μL of ethanol was added in liquid formulation with the average particle size of about 250 nm, whereas liquid formulations were not well dispersed in water when 6.25 and 9.5 μL of ethanol were added in the liquid formulation.

Meanwhile, each of the solubilizing compositions manufactured the same as in the above step (1) of Example 4 as a control group was added with an excessive amount of distilled water in place of ethanol. As a result, a gel with a strong viscosity was generated and it was shown to have an isotropic structure when observed under a polarized light microscope. In this case, the measurement of a particle size was not possible because the formulation was not dispersed in water.

EXAMPLE 5

Liquid Formulation Manufactured According to the Change in the Amount of a Solvent (2)

The liquid formulations and dispersed liquid were prepared the same as in the step (1) of the Example 4 and their particle size and polydispersity were measured by the same methods in the Example 4 with the exception that 14.5, 22.0, 34.0, 57.5, and 129.5 μL of PEG400, respectively, was added instead of ethanol to each 11.5 mg of the solubilizing compositions obtained in the above step (1). In this case, the above formulations were well dispersed in water and the particle size was about 300 nm.

EXAMPLE 6

Liquid Formulation Manufactured According to the Change in the Amount of a Solvent (3)

The liquid formulations and dispersed liquid were prepared the same as in the step (1) of the Example 4 and their particle size and polydispersity were measured by the same methods in the Example 4 with the exception that 14.5, 22.0, 34.0, 57.5, and 129.5 μL of propylene glycol, respectively, was added instead of ethanol to each 11.5 mg of the solubilizing compositions obtained in the above step (1). In this case, the above formulations were well dispersed in water and the particle size was about 300 nm.

The results of the Examples 4–6 are summarized in the following Table 2.

TABLE 2

| Amount of Solvent (μL) | Solvents | | |
|---|---|---|---|
| | Ethanol | PEG400 | Propylene glycol |
| | Average Particle Size (nm)/Polydispersity | | |
| 0 (control) | Not dispersed | Not dispersed | Not dispersed |
| 6.25 | Not dispersed | — | — |
| 9.5 | Not dispersed | — | — |
| 14.5 | 253.6/0.191 | 278.0/0.290 | Not dispersed |
| 22.0 | 254.4/0.105 | 288.4/0.377 | Not dispersed |
| 34.0 | 271.9/0.175 | 294.2/0.393 | 312.1/0.257 |
| 57.5 | 296.7/0.246 | 268.0/0.378 | 295.3/0.222 |
| 129.5 | 296.8/0.191 | 310.3/0.394 | 284.8/0.224 |

EXAMPLE 7

Liquid Formulation Manufactured According to the Change in the Amount of an Emulsifier (4)

(1) Manufacturing Solubilizing Composition

One hundred milligram of monoolein and 15, 20, 25, 30, 35 and 40 mg each of $PEG_{2000}PE$ were added to about 1 mL of ethanol and dissolved completely. Ethanol in the mixture was evaporated by stirring under nitrogen atmosphere or by applying low pressure. Trace amount of ethanol still remaining in the above mixture did not affect the manufacturing of formulations.

(2) Manufacturing of Liquid Formulations and Property Analysis

In the solubilizing compositions in the above step (1), 115, 120, 125, 130, 135 and 140 mg of ethanol was added so that the final concentration of the ethanol in the resulting mixture can be about 50% (w/w). The mixture was shaken manually or set aside to be dissolved completely to prepare the liquid formulation. The size and polydispersity of the emulsion particles were measured after diluting the emulsion by adding 3 mL of distilled water with 2 μL of thus obtained liquid formulation.

The above liquid formulations were well dispersed in water when more than 20 mg of $PEG_{2000}PE$ was added in liquid formulation with the average particle size resulted of about 350 nm, whereas liquid formulations were not dispersed well in water when less than 20 mg of $PEG_{2000}PE$ was added.

Meanwhile, each of the solubilizing compositions manufactured the same as in the above step (1) of Example 7 as a control group was added with an excessive amount of distilled water. The resulting gel had a strong viscosity and was not dispersed well in water and also shown to have an isotropic structure when observed under a polarized light microscope.

EXAMPLE 8

Liquid Formulation Manufactured According to the Change in the Amount of an Emulsifier (5)

The liquid formulations and dispersed liquid were prepared the same as in the step (1) of the Example 7 and their particle size and polydispersity were measured by the same methods in the Example 7 with the exception that PEG400 was added as an organic solvent in place of ethanol. When the PEG400 was added less than 15 mg the formulations were not dissolved in water. When more than 15 mg of PEG400 was added, the above formulations were well dispersed and the particle size was about 400 nm.

EXAMPLE 9

Liquid Formulation Manufactured According to the Change in the Amount of an Emulsifier (6)

The liquid formulations and dispersed liquid were prepared the same as in the step (1) of the Example 7 and their particle size and polydispersity were measured by the same methods in the Example 7 with the exception that 269, 280, 292, 303, 315 and 327 mg of propylene glycol, respectively, was added as an organic solvent in place of ethanol. In this case, all the liquid formulations were well dispersed regardless of the amount of propylene glycol and the resulting particle size was about 350 nm.

The results of the Examples 7–9 are summarized in the following Table 3.

TABLE 3

| $PEG_{2000}PE$ (mg) | Solvents | | | |
|---|---|---|---|---|
| | Water(control) | Ethanol | PEG400 | Propylene glycol |
| | Average Particle Size (nm)/Polydispersity | | | |
| 15 | Not dispersed | Not dispersed | Not dispersed | 346.1/0.533 |
| 20 | Not dispersed | Not dispersed | 421.8/0.579 | 365.6/0.404 |
| 25 | Not dispersed | 373.3/0.643 | 390.5/0.316 | 381.0/0.443 |
| 30 | Not dispersed | 344.2/0.689 | 435.8/0.659 | 367.9/0.341 |
| 35 | Not dispersed | 363.7/0.292 | 405.7/0.801 | 340.7/0.473 |
| 40 | Not dispersed | 377.5/0.545 | 397.8/0.511 | 370.9/0.606 |

EXAMPLE 10

Liquid Formulation Manufactured According to the Change of an Emulsifier (1)

One hundred milligrams of monoolein and 20 mg of Pluronic F-68 were added into about 1 mL of ethanol, dissolved completely and then solubilizing composition was obtained by removing the ethanol as described in the Example 1. After adding 120 mg of ethanol into the solubilizing compositions in the above step (1), the mixture was shaken manually or set aside to be dissolved completely to prepare the liquid formulation. The size and polydispersity of the emulsion particles were measured after diluting the emulsion by adding 3 mL of distilled water with 2 μL of thus obtained liquid formulation. The above formulation was well dispersed in water and the results showed the average particle size was 287.3 nm and the polydispersity was 0.273. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope.

EXAMPLE 11

Liquid Formulation Manufactured According to the Change of an Emulsifier (2)

One hundred milligrams of monoolein and 20 mg of Pluronic F-68 were added into about 1 mL of ethanol, dissolved completely and then solubilizing composition was obtained by removing the ethanol as described in the Example 1. After adding 120 mg of propylene glycol into the solubilizing compositions in the above step (1), the mixture was shaken manually or set aside to be dissolved completely to prepare the liquid formulation. The size and polydispersity of the emulsion particles were measured after diluting the emulsion by adding 3 mL of distilled water with 2 μL of thus obtained liquid formulation. The above formulation was well dispersed in water and the results showed the average particle size particle size was 265.0 nm and the polydispersity was 0.259.

EXAMPLE 12

Liquid Formulation Manufactured According to the Change of an Emulsifier (3)

Solubilizing composition was manufactured as in the Example 10 with the exception that 15 mg of dinonanoylphosphatidylcholine (DNPC) was added in place of Pluronic F-68, and liquid formulation was subsequently obtained by adding ethanol to the solubilizing composition. The size and polydispersity of the emulsion particles were measured after diluting the emulsion by adding 3 mL of distilled water with 2 μL of thus obtained liquid formulation. The above formulation was well dispersed in water and the results showed the average particle size particle size was 505.0 nm and the polydispersity was 0.422. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope.

EXAMPLE 13

Liquid Formulation Manufactured According to the Change of an Emulsifier (4)

Solubilizing composition was manufactured as in the Example 10 with the exception that 20 mg of Tween 20 was added in place of Pluronic F-68, and liquid formulation was subsequently obtained by adding ethanol to the solubilizing composition. The size and polydispersity of the emulsion particles were measured after diluting the emulsion by adding 3 mL of distilled water with 2 μL of thus obtained liquid formulation. The above formulation was well dispersed in water and the results showed the average particle size particle size was 264.5 nm and the polydispersity was 0.476. Meanwhile, the solubilizing composition manufactured the same as in the above as a control group was added with an excessive amount of distilled water. The resulting gel had a strong viscosity and was not dispersed well in water and also shown to have an isotropic structure when observed under a polarized light microscope.

EXAMPLE 14

Liquid Formulation Manufactured According to the Change of an Emulsifier (5)

Solubilizing composition was manufactured as in the Example 10 with the exception that 20 mg of Tween 80 was added in place of Pluronic F-68, and liquid formulation was subsequently obtained by adding ethanol to the solubilizing composition. The size and polydispersity of the emulsion particles were measured after diluting the emulsion by adding 3 mL of distilled water with 2 μL of thus obtained liquid formulation. The above formulation was well dispersed in water and the results showed the average particle size particle size was 234.0 nm and the polydispersity was 0.305. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope.

EXAMPLE 15

Liquid Formulation Manufactured According to the Change of an Emulsifier (6)

Solubilizing composition was manufactured as in the Example 10 with the exception that 20 mg of cremophor EL (EL) was added in place of Pluronic F-68, and liquid formulation was subsequently obtained by adding ethanol to the solubilizing composition. The size and polydispersity of the emulsion particles were measured after diluting the emulsion by adding 3 mL of distilled water with 2 μL of thus obtained liquid formulation. The above formulation was well dispersed in water and the results showed the average particle size was 218.4 nm and the polydispersity was 0.330. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope.

EXAMPLE 16

Liquid Formulation Manufactured According to the Change of an Emulsifier (7)

Solubilizing composition was manufactured as in the Example 10 with the exception that 20 mg of dioleyltrimethylammoniumpropane (DOTAP) was added in place of Pluronic F-68, and liquid formulation was subsequently obtained by adding ethanol to the solubilizing composition. The size and polydispersity of the emulsion particles were measured after diluting the emulsion by adding 3 mL of distilled water with 2 μL of thus obtained liquid formulation. The above formulation was well dispersed in water and the results showed the average particle size particle size was 397.1 nm and the polydispersity was 0.439. Meanwhile, the solubilizing composition manufactured the same as in the above as a control group was added with an excessive amount of distilled water. The resulting gel had a strong viscosity and was not dispersed in water and also have an isotropic structure when observed under a polarized light microscope. The results of the Examples 10–16 are summarized in the following Table 4.

TABLE 4

| Emulsifier | Organic Solvent | Particle size (nm) | Polydispersity |
|---|---|---|---|
| Pluronic F-68 | Ethanol | 287.3 | 0.273 |
|  | Propylene Glycol | 265.0 | 0.259 |
| DNPC | Ethanol | 505.0 | 0.422 |
| Tween 20 | Ethanol | 264.5 | 0.476 |
| Tween 80 | Ethanol | 234.0 | 0.305 |
| Cremophor EL | Ethanol | 218.4 | 0.330 |
| DOTAP | Ethanol | 397.1 | 0.439 |
| Control Group* |  | Not dispersed | |

*All the control groups (when solubilizing compositions were to be directly dispersed in water) were not dispersed regardless of the kind of an emulsifier being used.

EXAMPLE 17

Liquid Formulation Manufactured According to the Use of a Composite Emulsifiers (1)

(1) Manufacturing Solubilizing Composition

Sixty-five milligrams of monoolein, 35 mg of egg phosphatidyl choline (lecithin, PC) and 10 mg of Pluronic F-127 were added to about 1 mL of ethanol and dissolved completely. The above mixture was shaken manually or set aside to be dissolved completely to prepare the liquid formulation. Trace amount of ethanol still remaining in the above mixture did not affect the manufacturing of formulations.

(2) Manufacturing of Liquid Formulations and Property Analysis

After adding 120 mg of ethanol into the solubilizing compositions in the above step (1), the mixture was shaken manually or set aside to be dissolved completely to prepare the liquid formulation. The size and polydispersity of the emulsion particles were measured after diluting the emulsion by adding 3 mL of distilled water with 2 μL of thus obtained liquid formulation. The above formulation was well dispersed in water and the results showed that the average particle size was 351.6 nm and the polydispersity was 0.505. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope. The average particle size was about 2117.1 nm and the polydispersity was 1.000.

EXAMPLE 18

Liquid Formulation Manufactured According to the Use of Composite Emulsifiers (2)

One hundred milligrams of monoolein, 15 mg of $PEG_{2000}PE$ and 15 mg of dimyristylphosphatidylcholine (DMPC) were added to about 1 mL of ethanol and manufactured the solubilizing composition as in the Example 17. After adding 120 mg of ethanol into the solubilizing compositions, the mixture was shaken manually or set aside to be dissolved completely to prepare the liquid formulation. The size and polydispersity of the emulsion particles were measured after diluting the emulsion by adding 3 mL of distilled water with 2 μL of thus obtained liquid formulation. The above formulation was well dispersed in water and the results showed that the average particle size was 486.7 nm and the polydispersity was 0.190. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope.

EXAMPLE 19

Liquid Formulation Manufactured According to the Use of A Composite Emulsifiers (3)

One hundred milligrams of monoolein, 15 mg of Pluronic F-127 and 15 mg of Tween 20 were added to about 1 mL of ethanol and manufactured the solubilizing composition as in the Example 17. After adding 120 mg of ethanol into the solubilizing compositions, the mixture was shaken manually or set aside be dissolved completely to prepare the liquid formulation. The size and polydispersity of the emulsion particles were measured after diluting the emulsion by adding 3 mL of distilled water with 2 μL of thus obtained liquid formulation. The above formulation was well dispersed in water and the results showed that the average particle size was 275.8 nm and the polydispersity was 0.223. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope. The results of the Examples 17–19 are summarized in the following Table 5.

TABLE 5

| Example | Solubilizing Composition | | Average Particle Size (nm)/ Polydispersity | |
|---|---|---|---|---|
| | | | Ethanol Added | No Ethanol Added (Control Group) |
| 17 | Monoolein: | 65 mg | 351.6/0.505 | 2117.1/1.000 |
| | Pluronic F-127: | 10 mg | | |
| | Egg PC: | 35 mg | | |
| 18 | Monoolein: | 100 mg | 486.7/0.190 | Not dispersed |
| | $PEG_{2000}PE$: | 15 mg | | |
| | DMPC: | 15 mg | | |
| 19 | Monoolein: | 100 mg | 275.8/0.223 | Not dispersed |
| | Pluronic F-127: | 15 mg | | |
| | Tween 20: | 15 mg | | |

EXAMPLE 20

Manufacturing of Liquid Formulation Containing Non-aqueous Compound

Three identical solubilizing compositions comprising 10 mg of monoolein, 2 mg of Pluronic F-127, 0.2 mg of oleyl alcohol and about 0.1 mL of ethanol were manufactured as in the Example 1. After adding 13 mg of ethanol, propylene glycol or PEG 400 into the solubilizing compositions, the mixture was shaken manually or set aside to be dissolved completely to prepare the liquid formulation. The size and polydispersity of the emulsion particles were measured after diluting the emulsion by adding 3 mL of distilled water with 2 μL of thus obtained liquid formulation. The above formulation was well dispersed in water and the results of the average particle size and the polydispersity measured are shown in the following Table 6. Meanwhile, the solubilizing composition manufactured the same as in the above as a control group was added with an excessive amount of distilled water. The resulting gel had a strong viscosity and was not dispersed in water and also shown to have an isotropic structure when observed under a polarized light microscope.

TABLE 6

| Solvent used | Average Particle Size (nm) | Polydispersity |
|---|---|---|
| Control Group | Not dispersed | Not dispersed |
| Ethanol | 202.8 | 0.227 |
| Propylene Glycol | 218.1 | 0.210 |
| PEG 400 | 209.5 | 0.127 |

EXAMPLE 21

Manufacturing of Liquid Formulation Containing a Pharmaceutical Compound (1)

One hundred milligrams of monoolein, 20 mg of Pluronic F-127 along with 0.5 mg of bromocresol green, were added to about 1.4 mL of ethanol to manufacture the solubilizing composition as in the step (1) of the Example 1. After adding 130 mg of ethanol into the solubilizing compositions, the mixture was shaken manually or set aside to be dissolved completely to prepare the liquid formulation. The size and polydispersity of the emulsion particles were measured after diluting the emulsion by adding 3 mL of distilled water with 2 µL of thus obtained liquid formulation. The above formulation was well dispersed in water and the results showed that the average particle size was 283.1 nm and the polydispersity was 0.583.

EXAMPLE 22

Manufacturing of Liquid Formulation Containing a Pharmaceutical Compound (2)

One hundred milligrams of monoolein, 20 mg of Pluronic F-127 along with 0.5 mg of rifampicin, were added to about 1.4 mL of ethanol and manufactured the solubilizing composition as in the step (1) of the Example 1. After adding 130 mg of ethanol into the solubilizing compositions, the mixture was shaken manually or set aside to be dissolved completely to prepare the liquid formulation. The size and polydispersity of the emulsion particles were measured after diluting the emulsion by adding 3 mL of distilled water with 2 µL of thus obtained liquid formulation. The above formulation was well dispersed in water and the results showed that the average particle size was 321.3 nm and the polydispersity was 0.367.

EXAMPLE 23

Manufacturing of Liquid Formulation Containing a Pharmaceutical Compound (3)

One hundred milligrams of monoolein, 20 mg of Pluronic F-127 along with 2 mg of bupivacaine were added to about 1.4 mL of ethanol and manufactured the solubilizing composition as in the step (1) of the Example 1. After adding 130 mg of ethanol into the solubilizing compositions, the mixture was shaken manually or set aside to be dissolved completely to prepare the liquid formulation. The size and polydispersity of the emulsion particles were measured after diluting the emulsion by adding 3 mL of distilled water with 2 µL of thus obtained liquid formulation. The above formulation was well dispersed in water and the results showed that the average particle size was 317.6 nm and the polydispersity was 0.563.

EXAMPLE 24

Manufacturing of Liquid Formulation Containing a Pharmaceutical Compound (4)

One hundred milligrams of monoolein, 20 mg of Pluronic F-127 along with 1 mg of paclitaxel were added to about 1.4 mL of ethanol and manufactured the solubilizing composition as in the step (1) of the Example 1. After adding 130 mg of ethanol into the solubilizing compositions, the mixture was shaken manually or set aside to be dissolved completely to prepare the liquid formulation. The size and polydispersity of the emulsion particles were measured after diluting the emulsion by adding 3 mL of distilled water with 2 µL of thus obtained liquid formulation. The above formulation was well dispersed in water and the results showed that the average particle size was 0.329. The results of the Examples 21–24 are summarized in the following Table 7.

TABLE 7

| Pharmaceutical Compound | Average Particle Size (nm) | Polydispersity |
|---|---|---|
| Bromocresol green | 283.1 | 0.583 |
| Rifampicin | 321.3 | 0.367 |
| Bupivacaine | 317.6 | 0.563 |
| Paclitaxel | 196.6 | 0.329 |

As shown in the above Table 7, all of the particles were shown to have a size smaller than 350 nm regardless of the kinds of the pharmaceutical compounds, and thus the formulation of the present invention is proven to solubilize a water-insoluble pharmaceutical compound successfully.

EXAMPLE 25

Manufacturing of Powder Formulation via Lyophilization (1)

One hundred microliters of liquid formulation manufactured as in the Example 10 was added to 1 mL of 5% trehalose aqueous solution, dispersed by shaking manually and lyophilized to obtain the powder formulation. About 3 mg each of these powder formulations were redispersed in 3 mL of distilled water to measure the particle size and the polydispersity by using the same method in the Example 1. The results showed that the average particle size was 388.0 nm and the polydispersity was 0.386.

EXAMPLE 26

Manufacturing of Powder Formulation via Lyophilization (2)

One hundred microliters of liquid formulation manufactured as in the Example 11 was added to 1 mL of 5% trehalose aqueous solution, dispersed by shaking manually and lyophilized to obtain the powder formulation. About 3 mg each of these powder formulations were redispersed in 3 mL of distilled water to measure the particle size and the polydispersity by using the same method in the Example 1. The results showed that the average particle size was 395.6 nm and the polydispersity was 0.666.

The results of the Examples 25–26 are summarized in the following Table 8.

TABLE 8

| Example | Composition of Liquid Formulation used in manufacturing Powder Formulation | | Average Particle Size (nm) | Polydispersity |
|---|---|---|---|---|
| 25 | Monoolein: | 100 mg | 388.0 | 0.386 |
|  | Pluronic F-127: | 20 mg |  |  |
|  | Ethanol: | 120 mg |  |  |
| 26 | Monoolein: | 100 mg | 395.6 | 0.666 |
|  | Pluronic F-127: | 20 mg |  |  |
|  | Propylene Glycol: | 120 mg |  |  |

As shown in the above Table 8, all the particles of the powder formulations were shown to have a size smaller than 400 nm even after redispersion in distilled water, and thus the formulation of the present invention is proven to solubilize a water-insoluble pharmaceutical compound successfully.

EXPERIMENTAL EXAMPLE 1

Release Experiment 1 of a Pharmaceutical Compound

One hundred and forty milligrams of monoolein, 28 mg of Pluronic F-127 and 0.7 mg of rifampicin, were added to about 1.4 mL of ethanol to prepare the solubilizing composition as in the Example 1. After adding 180 mg of PEG 400 into the solubilizing compositions, the mixture was shaken manually or set aside to be dissolved completely to prepare the liquid formulation.

Dispersion was prepared by mixing 250 μL of the above liquid formulation with 1.75 mL of distilled water and shaken manually. The mixture was then added into a dialysis bag (MWCO=3,500, Spectra/Por$^R$, Spectrum Medical Industries, Inc., USA), both ends were tied with a closure, and placed into a 50 ml conical tube containing 10 ml of phosphate buffered saline (PBS, pH=7.4). The conical tube was placed in a 37° C. shaking water bath for the release experiment. The PBS solution located outside the dialysis tube was collected at regular intervals to analyze concentration of the pharmaceutical compound released from the dialysis bag by using Fluorescence spectroscopy ($\lambda_{ex}$=370 nm, $\lambda_{em}$=480 nm). An aqueous solution where 0.7 mg of rifampicin was dissolved in 2 mL of distilled water was used as a control. The result showed that more than 80% of the drug was released within 5 hr in a control group while the liquid formulation according to the present invention exhibited a sustained release pattern by releasing over 120 hr.

EXPERIMENTAL EXAMPLE 2

Release Experiment 2 of a Pharmaceutical Compound

Release experiment was performed using the liquid formulation manufactured the same as in the experimental Example 1 with the exception that 0.7 mg of bromocresol green was used in place of rifampicin. The released drug was collected from the PBS solution and subsequently analyzed for its absorbance at 617 nm. An aqueous solution, where 0.7 mg of bromocresol green was dissolved in 2 mL of distilled water, was used as a control. The result showed that more than 80% of the drug was released within 5 hr in a control group while the liquid formulation according to the present invention exhibited a sustained release pattern.

The results of the above experiments are summarized in the following Table 9.

TABLE 9

| Experimental Example | Composition of Liquid Formulation | | Release Pattern |
|---|---|---|---|
| 1 | Monoolein | 140 mg | Sustained Release |
|   | Pluronic F-127 | 28 mg | |
|   | Rifampicin | 0.7 mg | |
|   | Rifampicin | 0.7 mg | Fast Release |
| 2 | Monoolein | 140 mg | Sustained Release |
|   | Pluronic F-127 | 28 mg | |
|   | Bromocresol Green | 0.7 mg | |
|   | PEG 400 | 180 mg | |
|   | Rifampicin | 0.7 mg | Fast Release |

EXPERIMENTAL EXAMPLE 3

Stability Test of a Pharmaceutical Compound According to Storage Time (1)

The stability of the liquid formulations manufactured according to the Example 1 was tested by measuring the size and polydispersity of the dispersion made from the liquid formulations of the present invention. The formulation was dispersed in water immediately after the preparation and also after storing for 120 days at room temperature for the measurement The results are shown in the following Table 10.

TABLE 10

| | Average Particle Size (nm)/ Polydispersity | |
|---|---|---|
| | Immediately After Manufacture | 120 Days after Manufacture |
| Liquid Formulation of the Present Invention | 254.4/0.069 | 263.4/0.247 |

As shown in the above Table 10, the dispersion prepared from the formulation according to the present invention retained small particle size with a narrow distribution both immediately after and 120 days after the preparation.

EXPERIMENTAL EXAMPLE 4

Stability Test of a Pharmaceutical Compound According to the Period of Storage (2)

Liquid formulations containing rifampicin or bromocresol green were manufactured as in the above experimental Examples 1 and 2. The particle size and the polydispersity of the above manufactured liquid formulations were measured by dispersing them in distilled water immediately after the manufacture, and 30 days or 120 days after the manufacture. The results are shown in the following Table 11.

TABLE 11

| Composition of Liquid Formulation | | Average Particle Size (nm)/Polydispersity | | |
|---|---|---|---|---|
| | | 0 Day | 30 Days | 120 Days |
| Monoolein | 140 mg | 283.1/0.583 | 329.8/0.669 | 278.5/0.673 |
| Pluronic F-127 | 28 mg | | | |
| Bromocresol Green | 0.7 mg | | | |
| PEG 400 | 180 mg | | | |
| Monoolein | 140 mg | 321.3/0.367 | 275.1/0.340 | 245.2/0.345 |
| Pluronic F-127 | 28 mg | | | |
| Bromocresol Green | 0.7 mg | | | |
| PEG 400 | 180 mg | | | |

As shown in the above Table 11, the dispersion prepared from the formulation according to the present invention retained small particle size with a narrow distribution both immediately after and 120 days after the preparation.

As described above, the formulations according to the present invention can solubilize stably a given pharmaceutical compound and also generate homogeneous particles less than 500 nm when dispersed in water. Moreover, the formulations can be easily dispersed in water without any mechanical aid, and problems such as phase separation, hydrolysis and oxidation can be prevented thus being suitable for use in drug delivery system.

What is claimed is:

1. A solubilizing composition comprising 9~90% by weight of at least one monoglyceride compound, 0.01~90% by weight of at least one emulsifier, 0~50% by weight of at least one water-insoluble material, 0~90.9% by weight of organic solvent and 0~5% by weight of other additives; wherein the solubilizing composition comprises cubosome particles.

2. The solubilizing composition of claim 1, wherein said monoglyceride compound is a saturated or an unsaturated monoglyceride compound having carbon atoms of 10~22.

3. The solubilizing composition of claim 2, wherein said monoglyceride compound is monoolein, monopalmitolein, monomyristolein, monoeladin, or monoerucin.

4. The solubilizing composition of claim 1, wherein said emulsifier is phospholipid, a non-ionic surfactant, an anionic surfactant, a cationic surfactant or bile acid.

5. The solubilizing composition of claim 4, wherein said phospholipid is selected from the group consisting of a phosphatidylcholine (PC) and its derivative, a phosphatidylethanolamine (PE) and its derivative, a phosphatidylserine (PS) and its derivative, and a polymeric lipid wherein a hydrophilic polymer is conjugated to the lipid headgroup.

6. The solubilizing composition of claim 4, wherein said non-ionic surfactant is selected from the group consisting of a poloxamer, Pluronic, polyoxyethylene-polyoxypropylene copolymer, a sorbitan ester, Span, a polyoxyethylene sorbitan, Tween, a polyoxyethylene ether, and Brij.

7. The solubilizing composition of claim 4, wherein said anionic surfactant is selected from the group consisting of a phosphatidylserine (PS) and its derivative, a phosphatidic acid (PA) and its derivative, and sodium dodecyl sulfate (SDS).

8. The solubilizing composition of claim 4, wherein said cationic surfactant is selected from the group consisting of 1,2-dioleyl-3-trimethylammonium propane (DOTAP), dimethyldioctadecylammonium bromide (DDAB), N-[1-(1,2-dioleyloxy)propyl]-N,N,N-trimethylammonium chloride (DOTMA), 1,2-dioleyl-3-ethylphosphocholic acid (DOEPC) and 3β-[N-[(N',N'-dimethylamino)ethan]carbamoyl]cholesterol (DC-Chol).

9. The solubilizing composition of claim 4, wherein said bile acid is selected from the group consisting of cholic acid, its salt and derivatives; deoxycholic acid, its salt and derivatives; ursodeoxycholic acid, its salt and derivatives; chenocholic acid, its salt and derivatives; and lithocholic acid, its salt and derivatives.

10. The solubilizing composition of claim 1, wherein said organic solvent is selected from the group consisting of alcohol, ethyleneglycol, propylene glycol, polyethyleneglycol, acetonitrile, chloroform, benzene, toluene, dimethylsulfoxide, acetone, and mixtures thereof.

11. The solubilizing composition of claim 1, wherein said water-insoluble material is a hydrophilic, a hydrophobic or an amphiphilic compound.

12. The solubilizing composition of claim 1, wherein said at least one water-insoluble material is selected from the group consisting of antivirals, steroidal anti-inflammatory drugs (SAID), non-steroidal anti-inflammatory drugs (NSAID), antibiotics, antifungals, vitamins, hormones, retinoic acid, prostaglandins, prostacyclins, anticancer drugs, antimetabolitic drugs, miotics, cholinergics, adrenergic antagonists, anticonvulsants, antianxiety agents, major tranquilizers, antidepressants, anesthetics, analgesics, anabolic steroids, estrogens, progesterones, glycosaminoglycans, polynucleotides, immunosuppressants, and immunostimulants.

13. The solubilizing composition of claim 12, wherein said immunosuppressant is cyclosporin A.

14. The solubilizing composition of claim 12, wherein said anticancer drug is paclitaxel.

15. The solubilizing composition of claim 1, wherein said other additives are fatty acids, fatty acid esters, or fatty acid alcohols.

16. A method of preparing the solubilizing composition of claim 1, wherein said method comprises the steps of dissolving at least one monoglyceride compound, at least one emulsifier and at least one water-insoluble material in an organic solvent and removing the organic solvent.

17. A liquid formulation comprising 1~99% by weight of the solubilizing composition of claim 1 and 1~99% by weight of an organic solvent.

18. The liquid formulation according to claim 17, wherein said organic solvent is selected from the group consisting of alcohol, ethyleneglycol, propylene glycol, polyethyleneglycol, acetonitrile, chloroform, benzene, toluene, dimethylsulfoxide, acetone, and mixtures thereof.

19. The method of preparing a liquid formulation comprising 1~99% by weight of the solubilizing composition of claim 1 and 1~99% by weight of an organic solvent, wherein said method comprises the step of preparing homogeneous liquid formulation by mixing said composition with organic solvent.

20. A powder formulation prepared by lyophilization of the dispersion of the said liquid formulation of claim 17 along with 0~30% (w/v) of a cryoprotectant.

21. The powder formulation of claim 20 wherein said cryoprotectant is selected from the group consisting of a sugar, mannitol, trehalose, an amino acid, arginine, a protein, albumin, and mixtures thereof.

22. A method of manufacturing the powder formulation of claim 20, wherein said method comprises the steps of:
  (a) dispersing in excess water, a liquid formulation comprising 1~99% by weight of the solubilizing composition of claim 1 and 1~99% by weight of an organic solvent; and
  (b) lyophilizing said dispersed liquid in step (a) by selectively adding a cryoprotectant.

23. A water-insoluble solubilizing liquid formulation comprising 9~90% by weight of at least one monoglyceride compound, 0.01~90% by weight of at least one emulsifier, 0.001~50% by weight of at least one pharmaceutical compound, 9~90% by weight of an organic solvent and 0~5% by weight of other additives;
  wherein the water-insoluble solubilizing liquid formulation comprises cubosome particles.

24. The solubilizing liquid formulation according to claim 23, wherein said pharmaceutical compound is a hydrophilic, a hydrophobic or an amphiphilic compound.

25. The solubilizing liquid formulation according to claim 23, wherein said pharmaceutical compound is selected from the group consisting of antivirals, steroidal anti-inflammatory drugs (SAID), non-steroidal anti-inflammatory drugs (NSAID), antibiotics, antifungals, vitamins, hormones, retinoic acid, prostaglandins, prostacyclins, anticancer drugs, antimetabolitic drugs, miotics, cholinergics, adrenergic antagonists, anticonvulsants, antianxiety agents, major tranquilizers, antidepressants, anesthetics, analgesics, anabolic steroids, estrogens, progesterones, glycosaminoglycans, polynucleotides, immunosuppressants, and immunostimulants.

26. The solubilizing liquid formulation of claim 25, wherein said immunosuppressant is cyclosporin A.

27. The solubilizing liquid formulation of claim 25, wherein said anticancer drug is paclitaxel.

28. A method of manufacturing the solubilizing liquid formulation according to claim 23, wherein said method comprises the steps of:
  (a) dissolving at least one monoglyceride compound, at least one pharmaceutical compound along with at least one emulsifier in an organic solvent and removing the organic solvent; and
  (b) preparing a homogeneous liquid formulation by mixing said composition in the above step (a) with an organic solvent.

29. A solubilizing powder formulation manufactured by lyophilization of the dispersion of the said solubilizing liquid formulation according to claim 23 by adding with 0~10% (w/v) of a cryoprotectant.

30. A method of manufacturing the solubilizing powder formulation of claim 29, wherein said method comprises:

(a) dispersing in excess water, a water-insoluble solubilizing liquid formulation comprising 9~90% by weight of at least one monoglyceride compound, 0.01~90% by weight of at least one emulsifier, 0.001~50% by weight of at least one pharmaceutical compound, 9~90% by weight of an organic solvent and 0~5% by weight of other additives; and (b) lyophilizing said dispersed liquid in step (a) by selectively adding a cryoprotectant.

* * * * *

UNITED STATES PATENT AND TRADEMARK OFFICE
CERTIFICATE OF CORRECTION

PATENT NO. : 6,994,862 B2
DATED : February 7, 2006
INVENTOR(S) : Seo Young Jeong, Ick Chan Kwon and Hesson Chung

It is certified that error appears in the above-identified patent and that said Letters Patent is hereby corrected as shown below:

Column 19,
Line 26, "(DOEPC) and" should read -- (DOEPC), and --.

Column 20,
Line 10, "with organic" should read -- with said organic --.

Signed and Sealed this

Thirtieth Day of May, 2006

JON W. DUDAS
*Director of the United States Patent and Trademark Office*